United States Patent
Alonso et al.

(10) Patent No.: US 9,901,613 B2
(45) Date of Patent: Feb. 27, 2018

(54) COMPOSITIONS COMPRISING COMPLEXES OF PROANTHOCYANIDINS WITH PEA PROTEINS

(71) Applicant: NOVINTETHICAL PHARMA SA, Pambio Noranco, Lugano (CH)

(72) Inventors: Miguel Angel Alonso, Barcelona (ES); Marco Di Fulvio, Soriano nel Cimino (IT); Michele Di Schiena, Robecco sul Naviglio (IT)

(73) Assignee: NOVINTETHICAL PHARMA SA, Pambio Noranco (CH)

( * ) Notice: Subject to any disclaimer, the term of this patent is extended or adjusted under 35 U.S.C. 154(b) by 0 days.

(21) Appl. No.: 15/380,732

(22) Filed: Dec. 15, 2016

(65) Prior Publication Data

US 2017/0095528 A1    Apr. 6, 2017

Related U.S. Application Data

(63) Continuation of application No. 14/779,438, filed as application No. PCT/EP2014/056138 on Mar. 27, 2014, now abandoned.

(30) Foreign Application Priority Data

Mar. 28, 2013    (IT) .............................. MI2013A0476

(51) Int. Cl.

| | | |
|---|---|---|
| *A61K 36/00* | (2006.01) | |
| *A61K 38/16* | (2006.01) | |
| *A61K 36/87* | (2006.01) | |
| *A61K 31/353* | (2006.01) | |
| *A61K 36/22* | (2006.01) | |
| *A61K 36/45* | (2006.01) | |
| *A61K 36/48* | (2006.01) | |
| *A61K 45/06* | (2006.01) | |
| *A61K 9/00* | (2006.01) | |
| *A61K 47/14* | (2017.01) | |
| *A61K 47/22* | (2006.01) | |
| *A61K 47/36* | (2006.01) | |

(52) U.S. Cl.
CPC .......... *A61K 38/168* (2013.01); *A61K 9/0056* (2013.01); *A61K 9/0095* (2013.01); *A61K 31/353* (2013.01); *A61K 36/22* (2013.01); *A61K 36/45* (2013.01); *A61K 36/48* (2013.01); *A61K 36/87* (2013.01); *A61K 45/06* (2013.01); *A61K 47/14* (2013.01); *A61K 47/22* (2013.01); *A61K 47/36* (2013.01)

(58) Field of Classification Search
CPC ...................................................... A61K 36/00
See application file for complete search history.

(56) References Cited

U.S. PATENT DOCUMENTS

| | | |
|---|---|---|
| 2002/0001651 A1* | 1/2002 | Norris ................ A23C 9/1307 426/534 |
| 2006/0210697 A1 | 9/2006 | Mower |
| 2009/0117056 A1 | 5/2009 | Hodal et al. |
| 2009/0148397 A1 | 6/2009 | Rozhon et al. |
| 2012/0015078 A1 | 1/2012 | Boursier et al. |
| 2013/0203663 A1 | 8/2013 | Mager et al. |
| 2014/0037603 A1 | 2/2014 | Bolster et al. |
| 2014/0134206 A1 | 5/2014 | Khoo et al. |

FOREIGN PATENT DOCUMENTS

| | | | |
|---|---|---|---|
| EP | 1911457 A1 * | 4/2008 | .......... A23L 1/3056 |
| WO | 2004017979 A2 | 3/2004 | |
| WO | 2010114864 A1 | 10/2010 | |

OTHER PUBLICATIONS

International Preliminary Report on Patentability of PCT/EP2014/056138 dated Mar. 27, 2015.

* cited by examiner

*Primary Examiner* — Qiuwen Mi
(74) *Attorney, Agent, or Firm* — Silvia Salvadori, P.C.; Silvia Salvadori (57) ABSTRACT

Disclosed is a complex of pea protein and proanthocyanidins for use in the treatment of disorders caused by alterations of the intestinal epithelial tissue.

9 Claims, 9 Drawing Sheets

COMPOSITIONS COMPRISING COMPLEXES OF PROANTHOCYANIDINS WITH PEA PROTEINS

This Non-Provisional Application is a Continuation Application of U.S. Ser. No. 14/779,438 filed on Sep. 23, 2015, which is a National Stage of PCT/EP2014/056138 filed on 27 Mar. 2014, which claims priority to and the benefit of Italian Application No. MI2013A000476 filed on 28 Mar. 2013, the contents of which are incorporated herein by reference in their entireties.

The invention relates to complexes of proanthocyanidins with a vegetable protein and their use as active ingredients in compositions for the treatment of gastrointestinal disorders, in particular disorders caused by alterations of the intestinal epithelial tissue (simple non-ciliated cylindrical epithelium).

PRIOR ART

Diarrhoea is a symptom of many gastrointestinal disorders and is often incapacitating and dangerous, especially in children and the elderly. Acute diarrhoea is mainly caused by intestinal infections, but can also be due to the use of medicaments or radiotherapy and to other pathological conditions (diverticulitis, heavy-metal poisoning, intestinal ischaemia, allergies and intolerances).

Acute diarrhoea with an infectious cause is a serious problem in developing countries; it is believed to cause the death of at least 4 million children under 5 years old every year.

Chronic diarrhoea is generally due to irritable bowel syndrome, coeliac disease or inflammatory bowel diseases (Crohn's disease, ulcerative rectocolitis).

In view of their different etiologies, various treatment options are available, based on the administration of antibiotics/antibacterials, spasmolytics/anticholinergics, probiotics, or opioid receptor agonists. However, some of said treatments must be administered with great caution, because they do not act on the causal pathological process.

Complexes of tannins complexed with animal proteins and gelatins, in particular with gelatin of bovine origin, albumin, casein or ovalbumin, have been proposed for some time as effective remedies for gastrointestinal disorders.

For example, the use of said complexes in the treatment of the various forms of diarrhoea is disclosed in EP 1764105, EP 2526939, EP 2361623 and US 20090062191. Gelatin tannate has been available on the market for some time as a medical device for the treatment of acute diarrhoea.

Although the complexes known so far are effective and well tolerated, there is still a need for new complexes with improved characteristics in terms of efficacy, safety, organoleptic characteristics, stability, and compatibility with other ingredients of oral formulations. Moreover, the complexes known and available to date are obtained from protein materials of animal origin, with the consequent safety problems associated with the possible transmission of diseases such as BSE, or allergies, which are particularly common in the case of proteins derived from milk and eggs. Complexes with animal proteins can also give rise to ethical or religious problems in some patient populations.

There is consequently still a need for further treatments to replace or accompany those available today.

DESCRIPTION OF THE INVENTION

It has now surprisingly been found that the complex of proanthocyanidins with pea protein is particularly effective in the treatment of disorders caused by alterations of intestinal epithelial tissue (simple non-ciliated cylindrical epithelium). The complex of the invention is advantageous in terms of safety, because it is practically devoid of liver toxicity, unlike the tannins already used to treat diarrhoea and other gastrointestinal disorders.

"Disorders caused by alterations of the intestinal epithelial tissue" means the inflammatory bowel diseases (Crohn and ulcerative colitis), celiac disease, enteric bacterial and parasitic infections (i.e. enteropathogenic *Escherichia coli, Giardia lamblia* infection, *C. difficile* infection, etc.), irritable bowel syndrome and various other diseases.

"Complex" means a chemical entity derived from the interaction between functional groups present on the protein and on the polyphenol structure. Said interactions, mainly of an ionic nature (such as hydrogen bonds), give the complex or adduct different physicochemical and biological properties from those of the components of the complex or their physical mixture.

"Pea protein" means a powdered protein obtained by extraction from *Pisum sativum* seeds available on the market.

One commercially available product, for example, is supplied by Dal Cin Gildo S.p.A. The product is in form of a yellowish powder with a characteristic odour, which is poorly soluble in water.

The term "proanthocyanidins" refers to polyphenol compounds formed by the union of 2 to 8 catechin units. Proanthocyanidins are abundant in various plants, especially in grape skins and pips, lingonberries and bilberries, and some types of wood, such as quebracho wood. Proanthocyanidins, which belong to the family of condensed tannins, have a high level of antioxidant activity, and various studies have demonstrated their efficacy in reducing the blood pressure, reducing platelet aggregation and counteracting the progress or onset of disorders of the cardiovascular system. Proanthocyanidins also possess antibacterial, antiviral, anti-angiogenetic, antitumoral and chemopreventive properties. Various preparations of proanthocyanidins are available on the market, especially preparations of proanthocyanidins extracted from *Vitis vinifera*.

The pea protein and proanthocyanidin complex can be prepared by mixing an aqueous suspension of the protein with a solution of proanthocyanidins. In particular, the pea protein is suspended in water, preferably in the ratio of 1:20 w/v. A solution of proanthocyanidins obtained from grape pips is added to this suspension in the ratio of 1:10 w/v in water.

The ratio of pea protein to proanthocyanidins ranges between 1:0.1 and 1:2.5; it is preferably between 1:0.5 and 1:2; and more preferably of 1:1.5.

It can be useful to acidify the suspension of pea protein in water, for example with citric acid, ascorbic acid or other acids, to improve the solubility of the protein; the pH is between 3 and 5, preferably between 3.5 and 4.5.

The temperature can vary within a wide range during the preparation of the complex: preferably between 10° C. and 50° C., and more preferably between 20° C. and 40° C.

The complex is isolated by known methods, such as filtration, centrifugation, spray-drying, freeze-drying etc.

The complex can be dried under vacuum, in an airstream, in fluid-bed dryers, etc., at a temperature preferably ranging between 20° C. and 40° C.

The complex thus obtained is highly stable to environmental humidity, even at temperatures exceeding ambient temperature. The complex of the invention, either alone or combined with other active ingredients and/or excipients, can be formulated in administration forms suitable for the recommended uses.

Other active ingredients which can be advantageously combined with the complexes of the invention include antibiotics, antimotility agents, steroidal and non-steroidal anti-inflammatories, compounds for the treatment of gastrointestinal bloating (simethicone and the like), mesalazine, sucralfate, natural and synthetic polysaccharides such as pectins, chitosan (animal or vegetable), hyaluronic acid, guar gum, xanthan gum, animal gelatins, cellulose and hemicellulose and derivatives such as hydroxypropylcellulose, carrageenans, carbomers, and crosslinking/polymerising compounds such as ferulic acid; and probiotics, such as Lactobacilli, Bifidobacteria, yeasts and the like.

The complex of the invention is useful for the treatment and prevention of gastrointestinal disorders and other disorders originating in the gastrointestinal system and transferred to other systems, such as the urogenital system. The complex of the invention is also useful to prevent the proliferation of pathogens in the gastrointestinal system and their transfer to other systems of the human body through the tight intestinal junctions. The complex of the invention is also useful to protect the intestinal mucosa against chemical or physical agents which can reduce the functionality and natural regeneration of the intestinal epithelium, and to reduce the paracellular flow of pathogens through the intestinal walls.

Examples of suitable forms of administration include capsules, tablets, solutions, suspensions, granules, gels, etc. Examples of other active ingredients with which the pea protein and proanthocyanidin complex can be combined include antibiotics, antimotility agents, anti-inflammatories, compounds for the treatment of gastrointestinal flatulence, prebiotics, probiotics, etc.

In view of its substantial absence of toxicity, the pea protein and proanthocyanidin complex can be administered several times a day at doses ranging from 50 mg to 6000 mg/day.

In particular, the proanthocyanidin and pea protein complex, in addition to being very effective and safe, is stable to hydrolysis and oxidation of the proanthocyanidin component.

The examples below illustrate the invention in greater detail.

Example 1

Preparation of Complex

A) 10 g of pea protein (Dal Cin Gildo S.p.A.) is suspended in 200 g purified water. The pH of the suspension is adjusted from pH 6.3 to pH 4 with anhydrous citric acid, 20% sol. w/v in water. The suspension is left under stirring for 3 hours, and the temperature is increased to 30° C.

B) 10 g of proanthocyanidins (Grape Seed Dry Extract (r), Indena Spa) is dissolved in 100 ml of purified water; the solution is prepared shortly before use, adjusting the pH from 6.7 to 4 with anhydrous citric acid, 20% sol. w/v in water, and heated to 30° C.; the dark red solution is added in portions to suspension A), still under stirring.

The complex in homogenous suspension that immediately forms is dark red, while the aqueous solution is reddish.

The suspension is kept under stirring for 3 hours, leaving the temperature to fall to 20° C.

Stirring is stopped and the suspension is left to stand for a further 8 hours, during which time it rapidly decants. The suspension is filtered through paper at low pressure.

The solid is washed with 100 ml of purified water acidified to pH 4 with a citric acid solution in 20 ml portions, aspirating thoroughly each time; the last wash is practically colourless. The solid is stove-dried at 35-40° C. until it reaches a constant weight.

Yield: 14.5 g; a brick-red, odourless, practically tasteless solid.

Analysis Data

Figure 1:
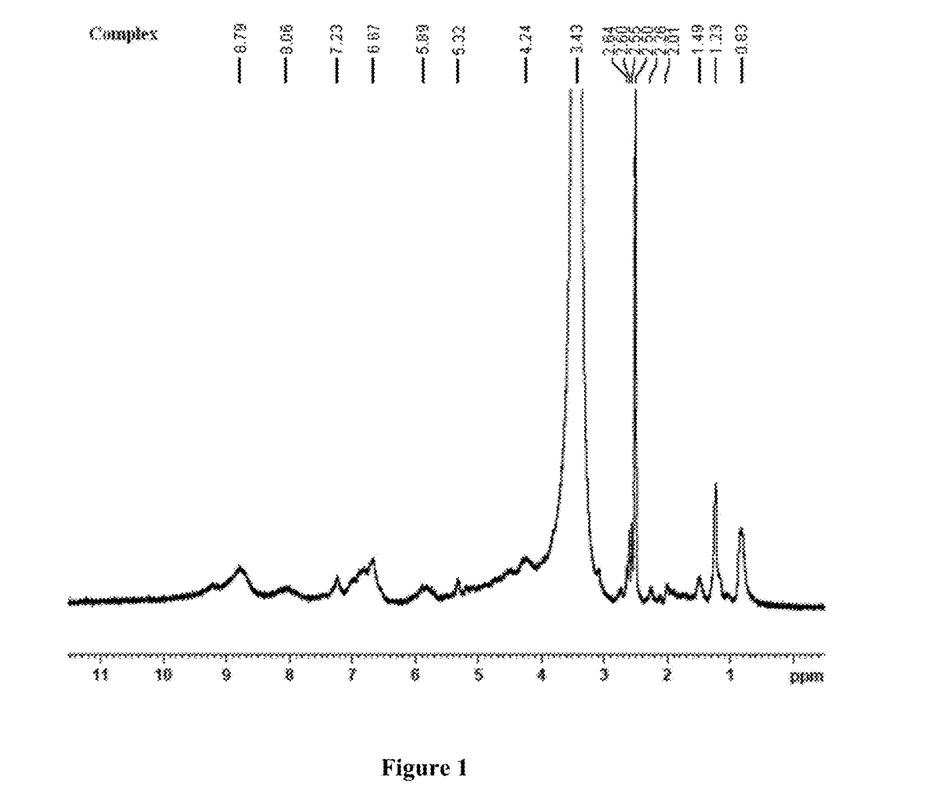
FIG. 1 shows the $^1$H NMR spectrum of the complex.

FIG. 1 shows the $^1$H NMR spectrum of the complex characterised by broadened signals in the region at $\delta$ 7.0, attributable to the aromatic protons of the proanthocyanidins.

The formation of a complex deriving from the chemical interaction between the protein component and the polyphenol component is demonstrated by the 2D DOSY (Diffusion Ordered Spectroscopy) NMR technique.

Figure 2:
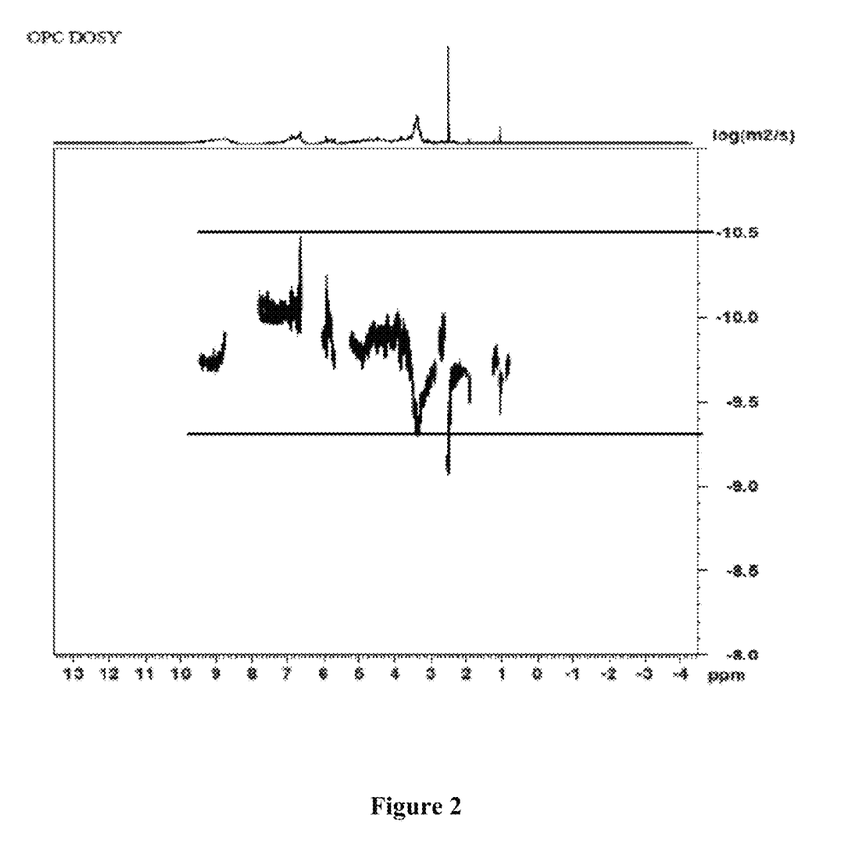
FIG. 2 shows the NMR spectrum recorded for proanthocyanidin obtained from *Vitis vinifera*.
Figure 3:
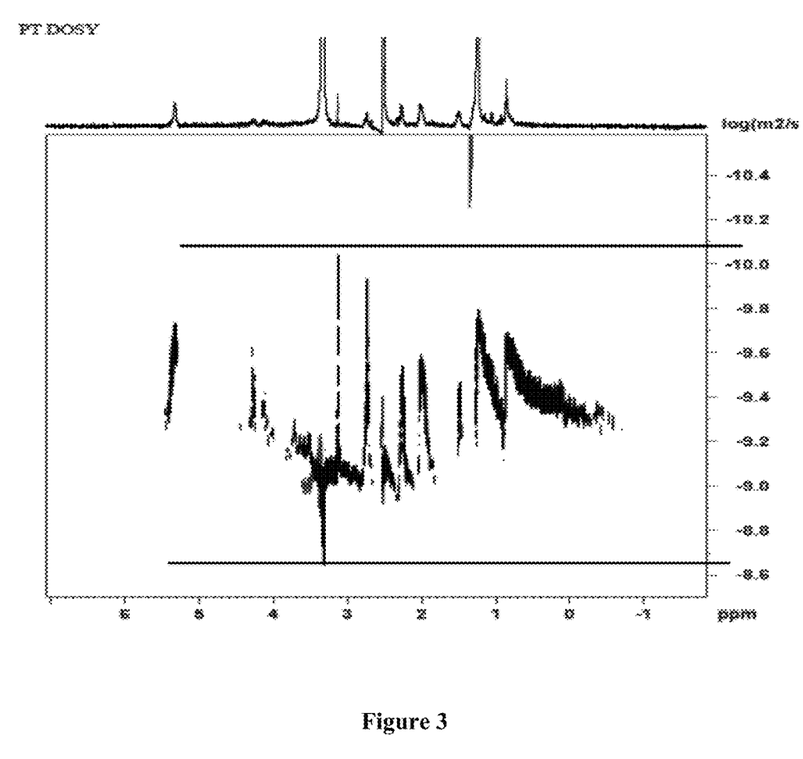
FIG. 3 shows the NMR spectrum recorded for proanthocyanidin obtained from pea protein.
Figure 4:
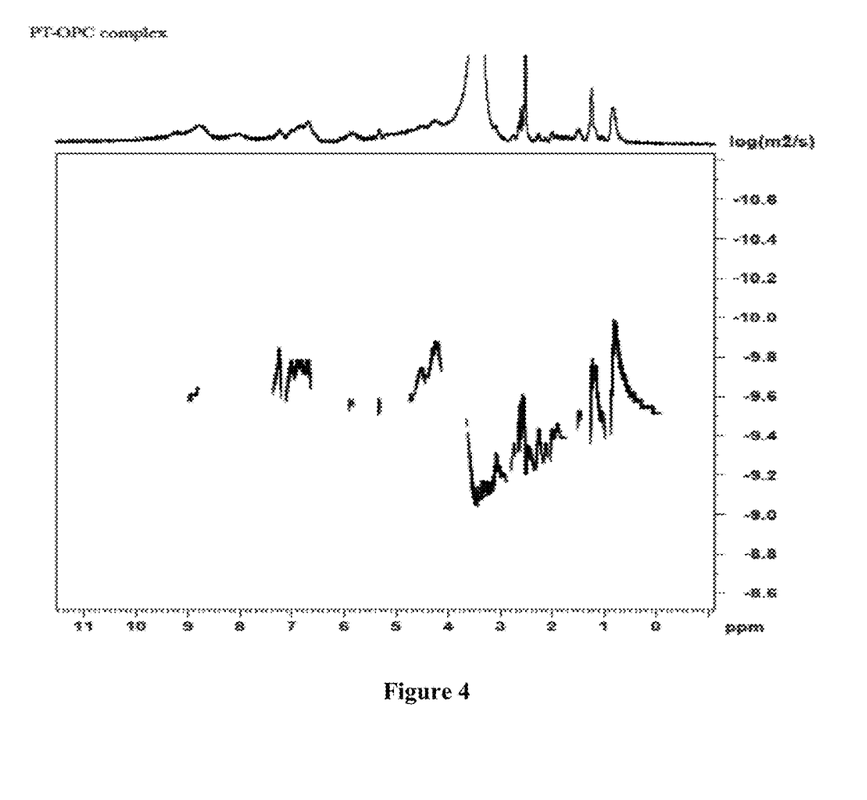
FIG. 4 shows the NMR spectrum recorded for prantho­cyanidin obtained from the complex of the invention.

The spectrum has a horizontal axis (T2) which relates to the resonance frequencies of the proton ($\delta$ or ppm), and a vertical axis (T1) which presents the diffusion parameter.

FIGS. 2, 3 and 4 show the spectra recorded for proanthocyanidin obtained from *Vitis vinifera*, pea protein, and the complex of the invention, respectively.

Signals distributed between the values in log(m2/s) (T1) of −9.2 and −10.5 can be observed in the spectrum of proanthocyanidin obtained from *Vitis vinifera*.

Conversely, the 2D DOSY spectrum of pea protein presents signals with T1 values between −8.7 and −10.1. The complex has a different behaviour from the preceding ones, with signals ranging between −9.1 and 10.0.

This indicates that an interaction exists between the species to form a different situation from the components. It is suggested that the interaction between protein and proanthocyanidin causes modifications to the protein structure, making it more compact and consequently obtaining a different diffusion coefficient.

HPLC gel-permeation assays were also performed. Isocratic elution was carried out with a mobile system formed by water, 0.1% formic acid and 3% methanol (flow rate of 1 mL/min., ELSD 60° C., 1.2 bar N2), stationary phase Tosohaas TSK G5000 PWXL 7.8×300 mm.

Figure 5:
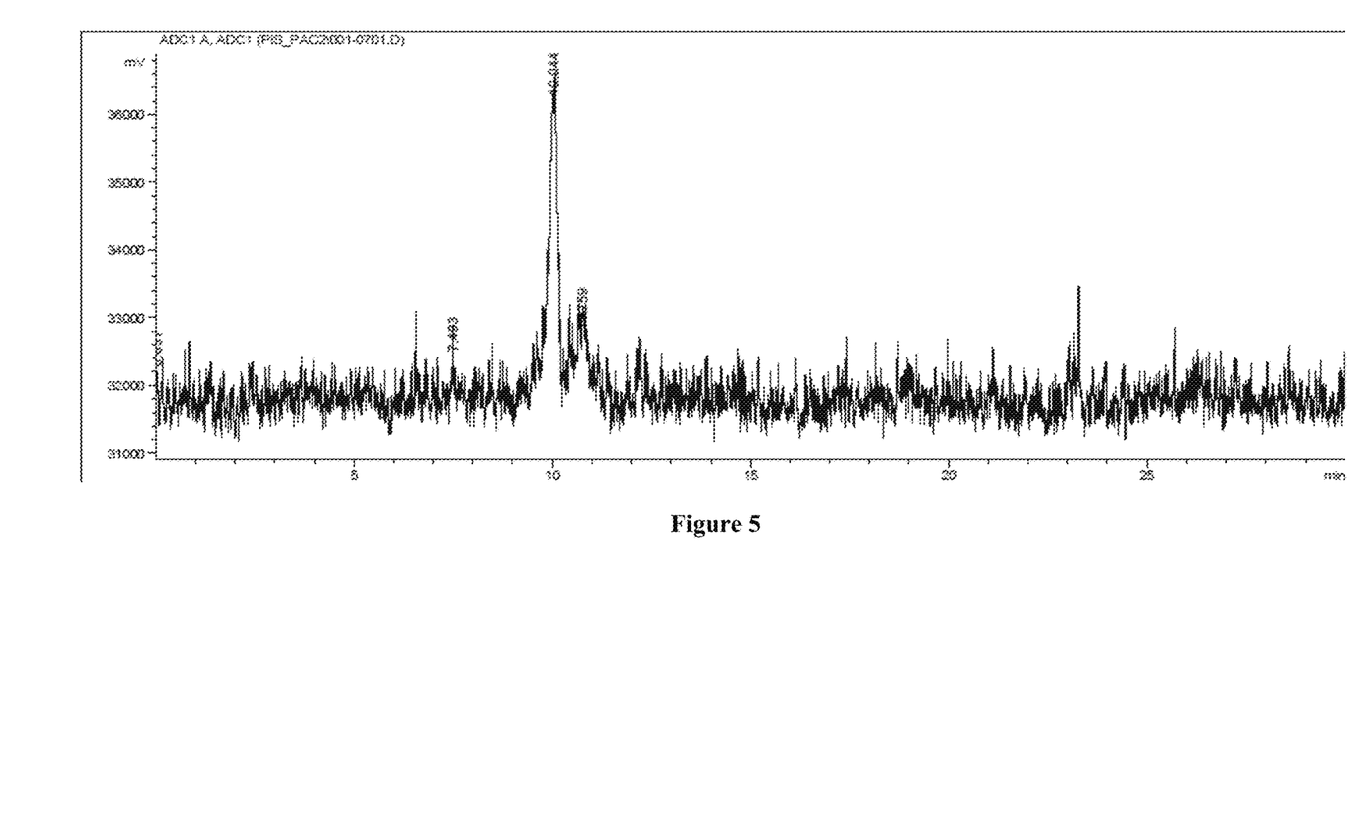
FIG. 5 shows the HPLC gel-permeation assay of the interaction of the pea protein mixture.
Figure 6:
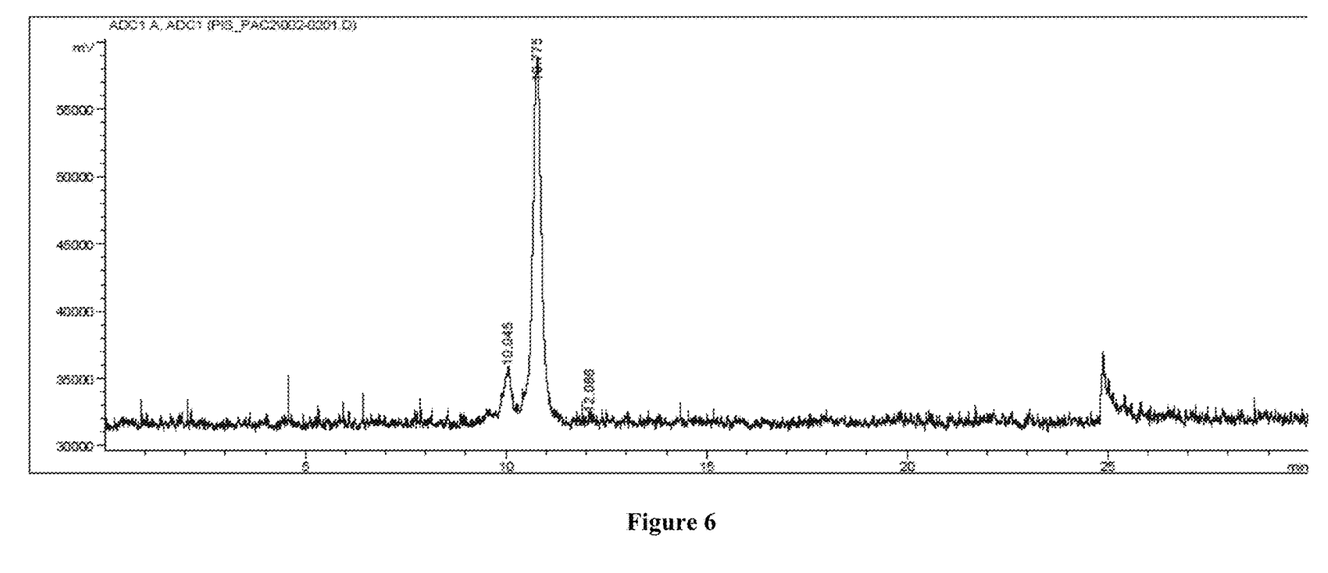
FIG. 6 shows the HPLC gel-permeation assay of black grape extract.

The chromatograms show the interaction between protein and proanthocyanidin. In particular, the chromatogram of the pea protein mixture (FIG. 5) clearly exhibits a prevalent peak at about 10 minutes, whereas the 95% black grape extract shows a prevalent peak at nearly 11 minutes, and a smaller peak at about 10 minutes (FIG. 6).

Figure 7:
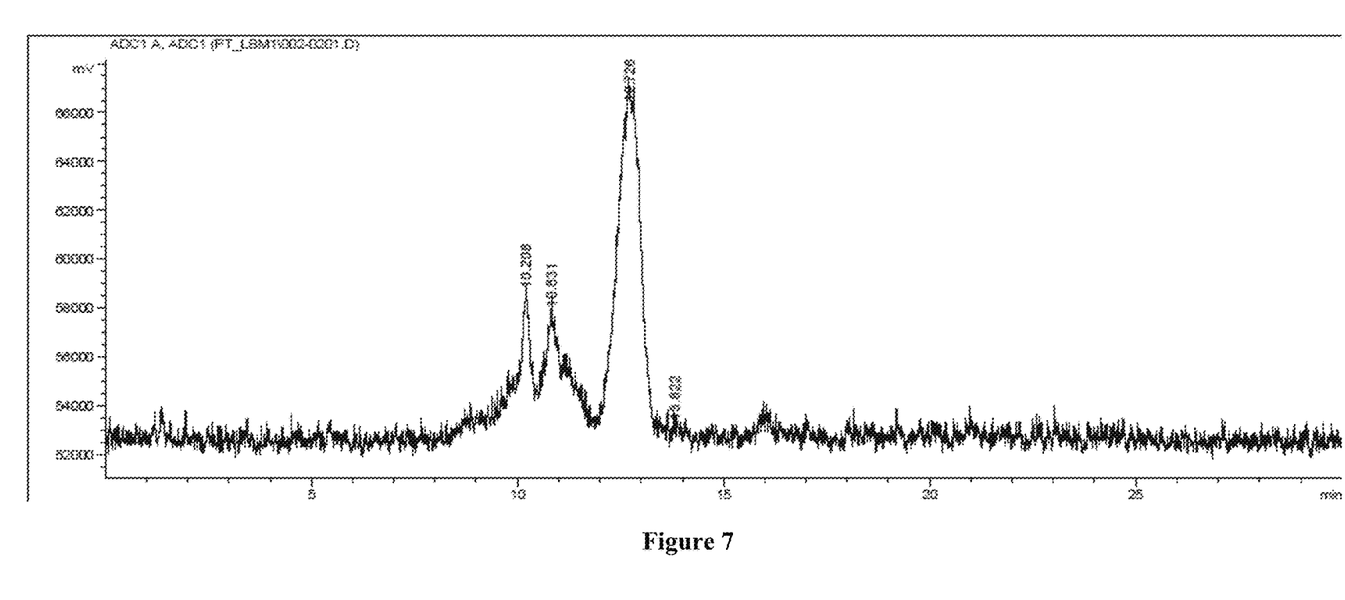
FIG. 7 shows the HPLC-gel permeation assay of the 50:50 complex.

The 50:50 complex shows a different chromatogram (FIG. 7), characterised by a peak at retention times exceeding about 13 minutes, confirming the NMR observations.

Example 2—Biological Tests In Vitro

The efficiency of the barrier and the chemical stability of the complex of the invention were evaluated by comparison with commercial gelatin tannate (Tasectan®) in the intestinal epithelium using the well-established predictive model of Caco-2 cells, a cell line of the intestinal epithelium deriving from a colorectal adenocarcinoma (ATCC HTB 37) (Cell. Biol. Toxicol. 2005, 21(1) 1-26).

The paracellular flow and the barrier permeability of the compounds tested were determined.

Paracellular flow was determined by measuring the transepithelial electrical resistance (TEER), which provides a direct measurement of the barrier function and is a further parameter of the integrity of the barrier at the tight junctions.

The permeability of the barrier was measured by determining the passage of the Lucifer Yellow dye (Le Ferrec et al., Altern Lab Anim 2001 November-December; 29(6):649-68; Hidalgo et al., Gastroenterology. 1989 March; 96(3): 736-49) after exposure to treatment with the compounds tested. This test was used to evaluate the integrity of the cell junctions in the presence of the substance tested. According to the technique described by Zucco et al., Altern. Lab Anim 2005 December; 33(6):603-18, the cell monolayer was incubated with the compounds tested at the concentration of 5 mg/ml at two different pH values, 7.4 and 8.3. The TEER was evaluated at time 0 and after 4 hours, and the flow of the Lucifer Yellow dye was monitored for two hours after treatment with the products tested.

The results proved the ability of the products tested to act as film-forming agents able to restore the barrier function and reduce its permeability so as to protect the intestinal mucosa and the structure of the tight cell junctions. The complex of the invention proved stable and active up to pH 8.3, unlike gelatin tannate, which is active at pH 7.4 but less active at pH 8.3, most likely due to hydrolysis of the tannins.

The proanthocyanidin complex is therefore more stable than the known gelatin tannate in the alkaline environment typical of the intestinal environment.

Example 3—Biological Tests In Vivo

The activity of the complex of proanthocyanidin obtained from *Vitis vinifera* and pea protein on the altered intestinal permeability and intestinal inflammation induced by lipopolysaccharide (LPS) was evaluated.

Groups of 8 male Wistar rats (200-225 g) have been used. After on overnight fast, the animals were injected intraperitoneally (IP) with 250 µL of sterile saline (NaCl 0.9%) containing or not (control) 1 mg/kg of lipopolysaccharide (LPS) from *E. Coli*. This dose has been previously shown to alter intestinal permeability and to release pro-inflammatory cytokines in the mucosa (TNFα, IL-1β, IFNγ (Moriez R. Am J Pathol. 2005; 167(4):1071-9). Six hours later, the animals have been sacrificed and strips of jejunum were used for evaluation of TEER and FITC-dextran paracellular permeability. Other segments were also collected for other parameters of mucosal inflammation (myeloperoxidase-MPO).

Six hours after LPS administration, the rats were sacrificed by cervical dislocation and the proximal part of the jejunum was removed. Jejunal strips were mounted in Ussing-type chambers (Physiologic Instruments, San Diego, Calif.). Both sides of each colonic layer will be bathed in Krebs-Henseleit buffer (Sigma) and oxygenated on a maintained temperature of 37° C. After 15 min for equilibrium, TEER was measured and 1 ml of buffer solution was replaced with physiological saline and 500 µl of FITC-dextran (4000 MW, 0.022 g/ml, Sigma) on mucosal side of each chamber. The fluorescence intensity generated was then measured 1 hour later.

Myeloperoxidase (MPO) Activity

MPO activity, a marker of polymorphonuclear neutrophil primary granules, was determined in proximal jejunum tissues, according to a modified method of Bradley et al., (1982). After sacrifice, colonic samples were removed and snap frozen until the MPO activity determination. Briefly, the colonic segments were ground by using a Polytron, before being submitted to 3 cycles of freezing-thawing and centrifugation. Supernatants were discarded and pellets were resuspended in a detergent that releases MPO. These suspensions were sonicated on ice, and then centrifuged another time. Pellets were discarded and supernatants were assayed spectrophotometrically for MPO activity and protein measurements. Protein concentration was determined by the method of Lowly (Bio Rad Detergent Compatible Protein Assay, BIO Rad, Ivry-France), and MPO activity will be expressed as U MPO/g of protein.

The experimental protocol was performed on groups of 8 male Wistar rats (Janvier S. A., Le Genest St. Isle, France) weighing 200-225 g at the time of experiments. The protocol consisted of a preventive oral administration of the complex of the invention at dose of 500 mg/kg or its vehicle (water) 2 h before ip injection of LPS from *E. coli* (1 mg/kg). These experiments were finally conducted on 3 separate groups of animals:

1 group as the control group (vehicle)—no LPS
1 group as the positive group (vehicle+LPS)
1 group compound CL-8 (500 mg/kg+LPS)

Intestinal Permeability:

Six hours after IP treatment with LPS, using chamber measurements jejunal permeability to FITC-dextran indicated that there was a huge increase in permeability to macromolecules, this increase was also significantly ($P \leq 0.05$) reduced by the compound of the invention (500 mg/kgPO) by 64.6%.

Figure 8:
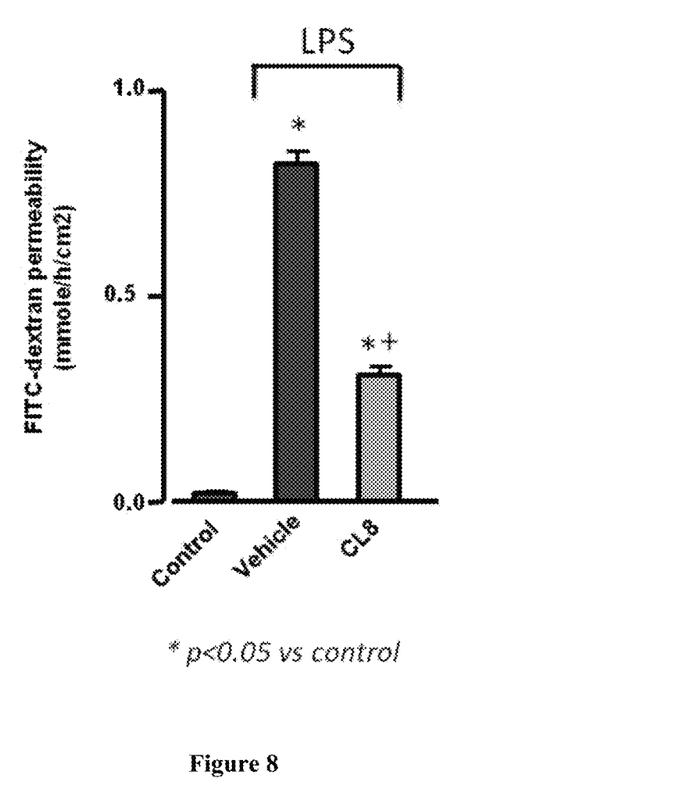
FIG. 8 shows the results of the influence of single oral treatment on LPS-induced increased jejunal permeability in rats.

The results are reported in FIG. 8 showing the influence of single oral treatment on LPS-induced increased jejunal permeability in rats (mean±SEM permeability n=2×8).

Mucosal Myeloperoxidase Activity (MPO):

In basal conditions, the jejunal mucosa MPO activity is very low (52±31 milliUnits/g. protein) and this tissular activity increased to 389±192 milliUnits/g. protein when measured 6 h. after LPS administration. The complex of the invention affected significantly ($P \leq 0.05$) this LPS-induced increase in jejunal MPO.

Figure 9:
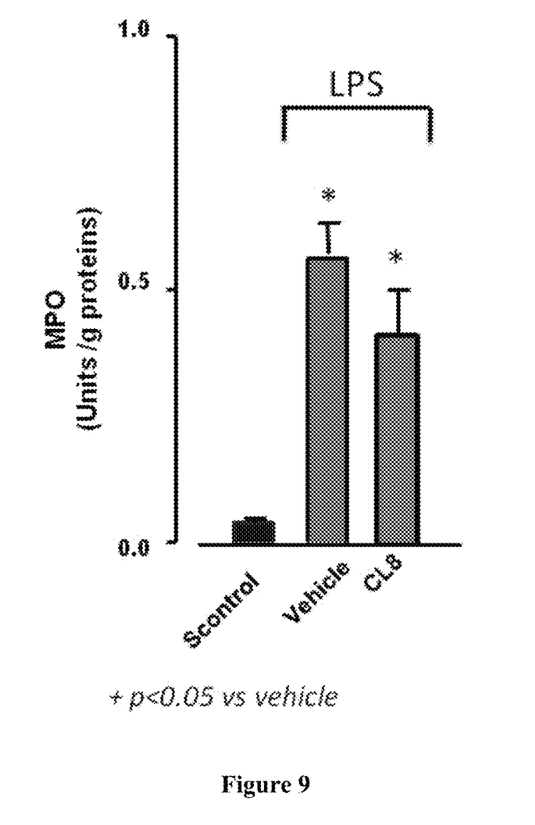
FIG. 9 shows the results of the influence of single oral treatment on LPS-induced mucosal MPO activity in rats.

The results are reported in FIG. 9 showing the influence of single oral treatment on mucosal MPO activity in rats (mean±SEM MPO n=8)).

Example 4—Pharmaceutical Formulation

Composition for the Treatment of Diarrhoea, 4 g Single-Dose Sachet

| | |
|---|---|
| Complex of pea protein with proanthocyanidins (example 1) | 0.500 g |

| | |
|---|---|
| Inulin | 1.500 g |
| Maltodextrin | 1.675 g |
| Ascorbic acid | 0.100 g |
| Monoglyceride (Rimulsoft super (V) | 0.150 g |
| Silicon dioxide (Aerosil 200) | 0.020 g |
| Stevioside (Stevia) | 0.015 g |
| E160a colouring (betacarotene) | 0.025 g |

The invention claimed is:

1. A method of treating disorders caused by inflammatory bowel diseases, celiac disease, enteric bacterial and parasitic infections and irritable bowel syndrome in a subject in need thereof with a complex comprising pea protein and proanthocyanidins, said method comprising:
   administering to said subject in need an effective amount of said complex; and
   treating said subject.

2. The method as claimed in claim 1, wherein the proanthocyanidins are extracted from *Vitis vinifera*, lingonberries or bilberries, or quebracho wood.

3. The method as claimed in claim 2, wherein the proanthocyanidins are extracted from *Vitis vinifera*.

4. The method as claimed in claim 1, wherein the ratio between pea protein and proanthocyanidins is between 1:0.1 and 1:2.5.

5. The method as claimed in claim 1 wherein the disorder is diarrhea.

6. The method as claimed in claim 1, comprising administering said complex in admixture with suitable carriers and optionally with other active ingredients suitable for treating disorders caused by inflammatory bowel diseases, celiac disease, enteric bacterial and parasitic infections and irritable bowel syndrome.

7. The method as claimed in claim 6, wherein said other active ingredients are selected from antibiotics, antimotility agents, steroidal and non-steroidal anti-inflammatories, compounds for the treatment of gastrointestinal bloating, mesalazine, sucralfate, pectins, chitosan, hyaluronic acid, guar gum, xanthan gum, animal gelatins, plant proteins, cellulose and hemicellulose, hydroxypropyl-cellulose, carrageenans, carbomers, ferulic acid, probiotics, gelatin tannate and electrolytes.

8. The method as claimed in claim 1, wherein said effective amount ranges from 50 mg to 6000 mg/day.

9. The method as claimed in claim 1, wherein said effective amount is 25 mg/kg.

* * * * *